US005741295A

United States Patent [19]
McEwen

[11] Patent Number: 5,741,295
[45] Date of Patent: *Apr. 21, 1998

[54] OVERLAPPING TOURNIQUET CUFF SYSTEM

[75] Inventor: James A. McEwen, 10551 Bamberton Drive, Richmond, Canada, V7A 1K6

[73] Assignee: James A. McEwen, Richmond, Canada

[ * ] Notice: The term of this patent shall not extend beyond the expiration date of Pat. No. 5,454,831.

[21] Appl. No.: 677,737

[22] Filed: Jul. 10, 1996

Related U.S. Application Data

[63] Continuation-in-part of Ser. No. 211,389, Jul. 25, 1994, Pat. No. 5,578,055, which is a continuation-in-part of Ser. No. 767,812, Sep. 30, 1991, Pat. No. 5,312,431.

[51] Int. Cl.$^6$ .................................................. A61B 17/00
[52] U.S. Cl. ........................................ 606/202; 606/201
[58] Field of Search ................................. 606/201–204; 602/13

[56] References Cited

U.S. PATENT DOCUMENTS

| | | |
|---|---|---|
| 2,031,870 | 4/1936 | Vertuno . |
| 2,444,161 | 6/1948 | Hanafin . |
| 2,943,859 | 5/1960 | Koski et al. . |
| 3,095,873 | 7/1963 | Edmunds . |
| 3,454,010 | 7/1969 | Lilligren et al. . |
| 3,587,584 | 6/1971 | Keller . |
| 3,633,567 | 1/1972 | Sarnoff . |
| 3,670,735 | 6/1972 | Hazlewood . |
| 3,901,225 | 8/1975 | Sconce . |
| 3,906,937 | 9/1975 | Aronson . |
| 4,469,099 | 9/1984 | McEwen . |
| 4,479,494 | 10/1984 | McEwen . |
| 4,605,010 | 8/1986 | McEwen . |
| 4,635,635 | 1/1987 | Roninette-Lehman . |
| 4,637,394 | 1/1987 | Racz et al. . |
| 4,716,906 | 1/1988 | Ruff . |
| 4,770,175 | 9/1988 | McEwen . |
| 4,771,790 | 9/1988 | Yamasawa et al. . |
| 4,869,265 | 9/1989 | McEwen . |
| 4,979,953 | 12/1990 | Spence . |
| 5,048,536 | 9/1991 | McEwen . |

(List continued on next page.)

FOREIGN PATENT DOCUMENTS

| | | |
|---|---|---|
| 15368 | 11/1971 | Australia . |
| 0 264 848 | 4/1988 | European Pat. Off. . |
| 695 842 | 12/1930 | France . |
| 2 204 388 | 5/1974 | France . |
| 458002 | 6/1950 | Israel . |
| 655 385 | 4/1979 | U.S.S.R. . |
| 2 253 789 | 9/1992 | United Kingdom . |

OTHER PUBLICATIONS

J.A. McEwen and G.F. Auchinleck, "Advances in Surgical Tourniquets" in Jaorn, vol. 36 (1982) pp. 889–896.

(List continued on next page.)

Primary Examiner—Glenn Dawson
Attorney, Agent, or Firm—Klarquist Sparkman Campbell Leigh & Whinston LLP

[57] ABSTRACT

An overlapping tourniquet cuff system for improved application of pressure to the limb, including an inflatable bladder; a sheath for containing the inflatable bladder wherein the sheath has a length sufficient to encircle the limb and overlap on itself in a substantially circumferential direction around the limb; a mechanism for securing the overlapped sheath around the limb; and a stiffening mechanism for superimposing over a region of the overlapped and secured sheath to constrain the shape of the sheath beneath the region when the bladder is inflated. The stiffening mechanism includes a securing mechanism for securing the overlapping sheath in a substantially circumferential direction around the limb independently of the sheath securing mechanism such that the sheath remains overlapped and secured in a substantially circumferential direction if the sheath securing mechanism is not engaged or becomes ineffective while the bladder is inflated. The system includes a pressure regulator assembly connected to the cuff for enabling the system to safely occlude flow in blood vessels in the encircled limb.

15 Claims, 6 Drawing Sheets

U.S. PATENT DOCUMENTS

| | | |
|---|---|---|
| 5,062,414 | 11/1991 | Grim . |
| 5,181,522 | 1/1993 | McEwen . |
| 5,254,087 | 10/1993 | McEwen . |
| 5,312,431 | 7/1994 | McEwen . |
| 5,385,538 | 1/1995 | Mann . |
| 5,449,379 | 9/1995 | Hadtke ............................ 606/703 |
| 5,454,831 | 10/1995 | McEwen ............................ 606/202 |

OTHER PUBLICATIONS

J.A. Shaw and D.J. Murray, "The Relationship Between Tourniquet Pressure and . . . " in J. Bone and Joint Surgery, vol. 64A (1982) pp. 1148–1152.

J.A. McEwen and R.W. McGraw, "An Adaptive Tourniquet for Improved Safety in Surgery" in IEEE Trans. Bio–Med Eng., vol. BME 29 (1982) pp. 122–128.

J.A. Shaw et al., "Guidelines for the Use of Digital Tourniquets . . . " in J. Bone & Joint Surgery, vol. 67A (1985) pp. 1086–1090.

A.C. McLaren and C.H. Rorabeck, "The Pressure Distribution Under Tourniquets" in J. Bone and Joint Surg. 67A (1985) pp. 433–438.

R.J. Newman and A. Muirhead, "A Safe and Effective Low Pressure Tourniquet" in J. Bone and Joint Surg., vol. 68B (1986) pp. 625–628.

S.E. Grice et al., "Intravenous Regional Anesthesia: Evaluation and Prevention of Leakage . . . " in Anesthesiology, vol. 65 (1986) pp. 316–320.

M.J. Breault et al., "Internal Pressure Distribution . . . " in Proc. Can. Med. Biol. Eng. Conf, (1989 Toronto) pp. 47–49.

J.A. McEwen et al., "Development and Evaluation of . . . " in Proc. 15th Can. Med. Biol. Eng. Conf. (1989 Toronto) pp. 107–108.

PCT International Search Report for International Application PCT/IE 92/00005, Jan. 5, 1993.

"CPC Couplings are Designed for Small Flexible Tubing Applications" (3–page publication) circa Jan. 1991.

OVERLAPPING TOURNIQUET CUFF SYSTEM

This application is a continuation-in-part of U.S. patent application Ser. No. 08/211,389 filed Jul. 25, 1994, having international filing date of Aug. 25, 1992, now U.S. Pat. No. 5,578,055, which is a continuation-in-part of U.S. patent application Ser. No. 07/767,812, filed Sep. 30, 1991, now U.S. Pat. No. 5,312,431. U.S. Pat. No. 5,312,431 is hereby incorporated by reference.

FIELD OF THE INVENTION

This invention pertains to cuffs for occluding flow in blood vessels in human limbs encircled by the cuffs. The invention particularly pertains to an overlapping occlusive cuff for improved application of pressure to a limb in order to facilitate the performance of a surgical procedure.

BACKGROUND OF THE INVENTION

The use of an inflatable cuff to occlude blood flow into a subject's limb, thereby providing a bloodless surgical field in the portion of the limb distal to the cuff over a time period suitably long for the performance of a surgical procedure, is well known in surgical practice. When employed to provide a bloodless surgical field, occlusive cuffs constitute one element of a surgical tourniquet system. Tourniquet systems typically include the following basic elements: a source of pressurized gas, an inflatable cuff for encircling a limb at a selected location, and a pressure regulating mechanism for controlling and maintaining the pressure of gas in the inflatable cuff and thus the pressure applied by the cuff to the limb which the cuff encircles. The recent advent of automatic tourniquet systems which employ digital electronic technology in the regulation of pressure and in the detection of certain hazardous conditions has led to significant improvements in the safety and accuracy of surgical procedures performed with an occlusive cuff applied proximally on a limb. These automatic tourniquet systems typically allow the surgeon to safely maintain a constant inflation pressure in the inflatable cuff which he or she estimates to apply pressures to the limb near the minimum required to safely occlude blood flow past the cuff. Recently, McEwen has described, in the U.S. patents cited below, improved automatic tourniquet systems which provide for sensing and regulation of the pressures actually applied to the limb by a cuff, in contrast to merely sensing and regulation of the inflation pressure in the cuff.

However, despite improvements in electronic pressure regulation and applied pressure sensing, major limitations exist with respect to safety and efficacy of occlusive cuffs used as part of automatic tourniquet systems. These limitations in prior art occlusive cuffs have persisted despite the increasing use of such cuffs in more demanding surgical procedures, particularly those involving the use of intravenous regional anesthesia (IVRA). In surgical procedures performed under IVRA, the occlusive cuff must be effective in preventing the flow of blood into the field of surgical dissection as well as preventing the premature release of potentially toxic intravenous anesthetics from the veins of the operative limb into the general circulation.

In the design of most prior art cuffs, little attention has been paid to the actual spatial distribution of pressures applied to the limb beneath the cuffs, in both a circumferential direction around the limb, and a direction along the longitudinal axis of the limb, when the cuffs are inflated to various inflation pressures. This lack of attention has largely been due to the lack of suitable pressure transducers for measuring the applied pressures. However, in connection with the present invention, the biomedical pressure transducer described by McEwen in U.S. Pat. No. 4,869,265 was used as a tool to evaluate the ranges of pressures applied to limbs by a large number of prior art cuffs, and was used as a tool in the development and evaluation of the improved occlusive cuff described hereunder.

By using the McEwen biomedical pressure transducer to measure the pressures applied by a representative selection of prior art cuffs which overlap on themselves around limbs, major variations were found in the pressures applied in a circumferential direction around the limbs beneath the cuffs. In particular, the greatest pressure variations were found in the region of the overlap, where the pressure actually applied to the limb could be much less than the inflation pressure of the cuffs, thus creating low pressure pathways longitudinally for arterial blood to enter the limb, or for IVRA anesthetic agents to exit the limb. Significantly, prior art cuffs having the greatest cross-sectional thicknesses were found to create the greatest pressure discontinuities in the region of the overlap, and cuffs having less cross-sectional thicknesses had less pressure variations circumferentially in the region of the overlap.

Also by using the McEwen biomedical pressure transducer, it was possible to measure the pressures applied to limbs beneath prior art cuffs in a longitudinal direction along the limb, between the proximal and distal edges of the cuff, at selected locations around the circumference. Again, significant differences in longitudinally applied pressures were found in prior art cuffs having different designs. Despite the information in the prior art that shows that the magnitude and distribution of pressures longitudinally beneath cuffs affects the probability of nerve injury beneath the cuff, little attention has previously been paid to the design of cuffs which permit optimal, desirable or selectable distributions of pressures to be applied in a longitudinal direction beneath such prior art cuffs.

Limitations also exist in the safety of prior art cuffs. At present, overlapping occlusive cuffs known in the prior art generally incorporate a single means of securing the cuff around the limb, with no additional securing means functioning independently to hold the cuff in place should the first securing means fail. No overlapping cuff in the prior art known to the applicant has a secondary circumferential securing means for independently securing the overlapped cuff circumferentially around a limb so that, if the primary means for securing the cuff around the limb were to fail for any of a variety reasons, the overlapped cuff would continue to apply pressure to the limb safely for the period required to complete a surgical procedure. Almost all cuffs in the prior art are designed to overlap on themselves around limbs, and use only a primary securing means, such as a pair of mating strips of hook and loop material, for securing circumferentially. Dual-bladder cuffs known in the prior art for use in IVRA do use two separate sets of securing means, but they are intended for securing two separate bladders arranged longitudinally on the limb; if one of these sets of securing means fails, the safety and efficacy of the inflatable bladder beneath that set of strips is significantly affected. The absence of an independent, secondary circumferential securing means in overlapping cuffs of the prior art significantly limits their safety, especially in critical surgical procedures where continued maintenance of a bloodless field is essential, and in other procedures involving IVRA where the cuff must keep anesthetic agents in the limb and out of systemic circulation for a specified minimum time period.

Overlapping occlusive cuffs in the prior art generally include a stiffener cut from a sheet of flexible thermoplastic material such as polyethylene, polypropylene, or nylon, to constrain the bladder of the cuff, reduce the tendency of the inflated cuff to roll distally down the limb, and direct inflation inwardly toward the limb when the bladder is pressurized. The choice of materials and the physical dimensions of prior art stiffeners have often been arbitrary, or based on factors other than how the physical characteristics of these stiffeners would affect the pressures applied longitudinally and circumferentially to underlying limbs. Also, such prior art stiffeners have generally been integrated physically into the cuffs during manufacture so that, in cross-section, the stiffeners represent one integral layer of a multi-layer structure. One result is that such prior art cuffs have significant cross-sectional thickness, producing significant applied pressure discontinuities in their overlapping regions, as described above. Such prior art cuffs are relatively rigid longitudinally across their width dimension, which limits their conformance to different limb shapes and can produce undesirable longitudinal pressure distributions. Also, such prior art cuffs are relatively rigid along their length, which increases the difficulty that clinical staff have in attempting to bend such cuffs around limbs to snugly encircle them.

Most cuffs of the prior art employ Luer-type connectors to attach the cuffs to tubing connected to the pressure regulators of automated tourniquet systems. These Luer-type connectors have inherent safety limitations, because they have no secondary locking mechanism and they permit easy, inadvertent gas leaks and disconnection as a result of rotation of the tubing with respect to the cuff. Further safety limitations of overlapping cuffs of the prior art related to the absence of markings on the cuffs indicating aspects of the recommended, safe and efficacious use of the cuffs. For example, most prior art cuffs do not include markings which provide guidance as to the best choice of cuff, taking into account the shape, circumference and available length of a patient's limb, nor are markings generally included to assist in the optimal setting of inflation pressure or proper cuff usage.

SUMMARY OF THE INVENTION

An object of the present invention is to provide an overlapping tourniquet cuff system having safety securing means for improved safety, comprising: an inflatable bladder for encircling and overlapping on itself around a limb, a sheath containing the bladder; a first sheath securing means carried by the sheath for securing the sheath around a limb, and a second sheath securing means for securing the overlapping sheath around the limb independently of the first sheath securing means, such that the bladder and sheath remain overlapped and secured if the first sheath securing means is not engaged or becomes ineffective while the bladder is inflated. A related object is to provide as part of the system pressure regulator means for supplying the bladder with a regulated source of pressurized gas such that, for example, the system occludes flow in blood vessels in the limb encircled by the sheath.

The applicant is aware of the following United State patents which are more or less relevant to the subject matter of the applicant's invention:

| U.S. Pat. No. | Issue Date | Inventor |
| --- | --- | --- |
| 5,254,087 | 10/19/93 | McEwen |
| 5,181,522 | 01/26/93 | McEwen |
| 5,048,536 | 09/17/91 | McEwen |
| 4,869,265 | 09/26/89 | McEwen |
| 4,770,175 | 09/13/88 | McEwen |
| 4,605,010 | 08/12/86 | McEwen |
| 4,479,494 | 10/30/84 | McEwen |
| 4,469,099 | 09/04/84 | McEwen |

BRIEF DESCRIPTION OF THE DRAWINGS

A specific embodiment of this invention has been chosen for purposes of illustration and description wherein.

Figure 4:
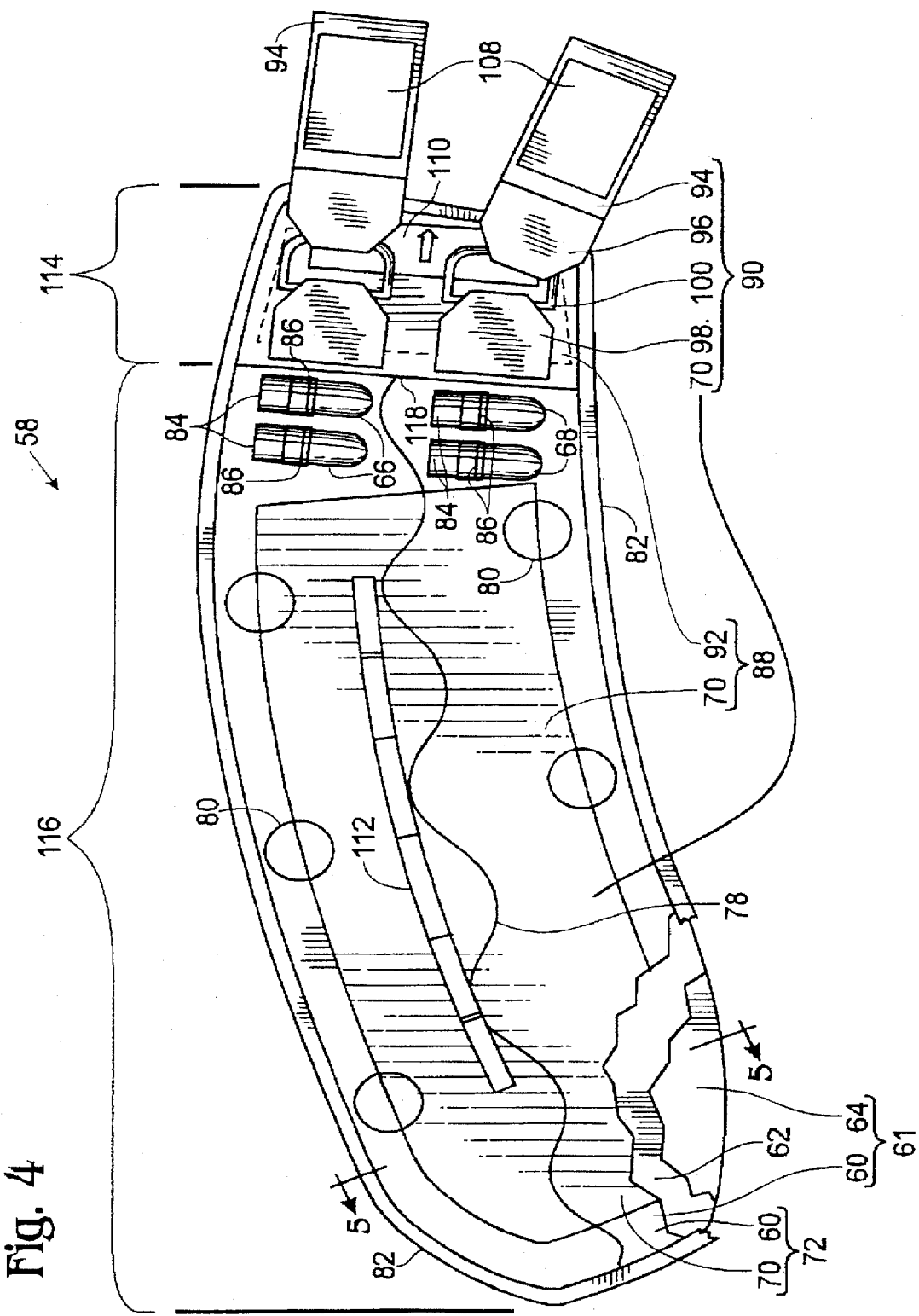

An alternate embodiment of this invention has been included for purposes of illustration and description wherein:

FIG. 4 is a plan view of the alternate embodiment of the improved overlapping occlusive cuff for application to a limb substantially conical in shape.

Figure 5:
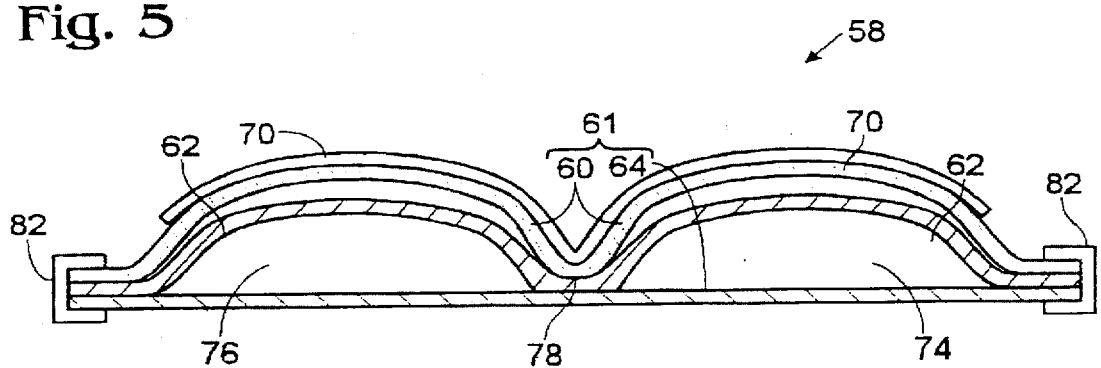

FIG. 5 is a cross-sectional view of the overlapping occlusive cuff of FIG. 4 taken along line 5—5.

Figure 6:
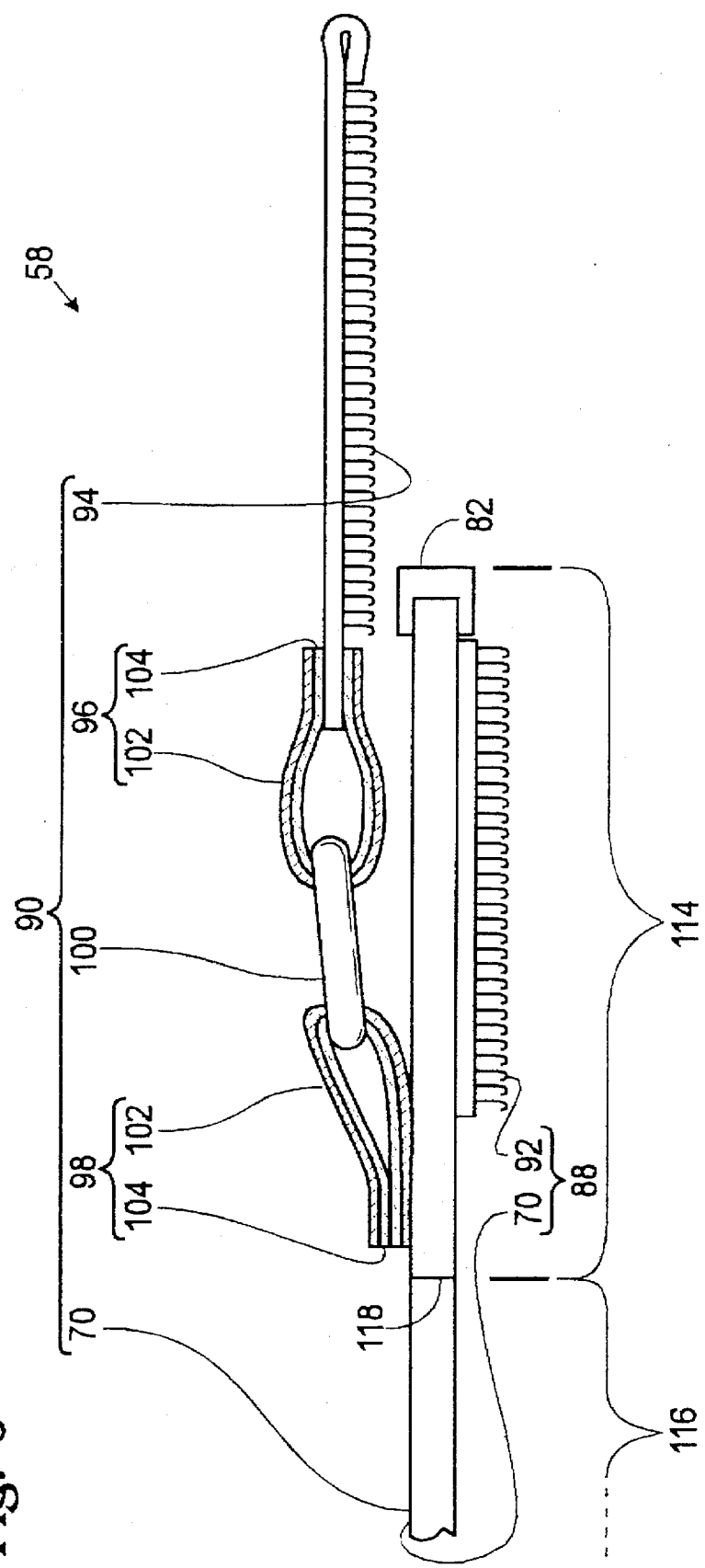

FIG. 6 is an exploded view of pivoting secondary safety securing means assembly of the cuff shown in FIG. 4.

Figure 7:
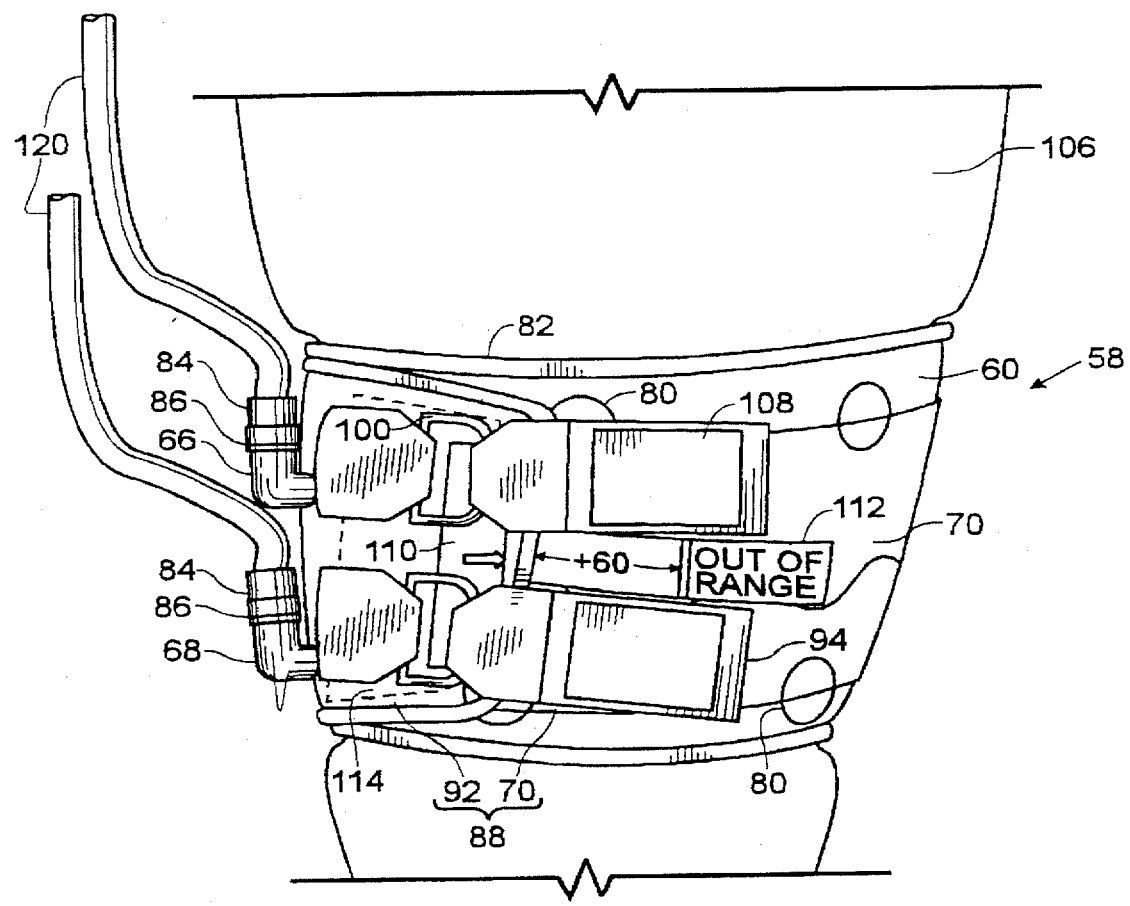

FIG. 7 is pictorial representation of the cuff, secondary safety securing means and markings shown in FIG. 4 as applied to a patient's limb.

DESCRIPTION OF THE SPECIFIC EMBODIMENT

The specific embodiment illustrated is not intended to be exhaustive or to limit the invention to the precise form disclosed. It is chosen and described in order to explain the principles of the invention and its application and practical use, and thereby enable others skilled in the art to utilize the invention.

Figure 1:
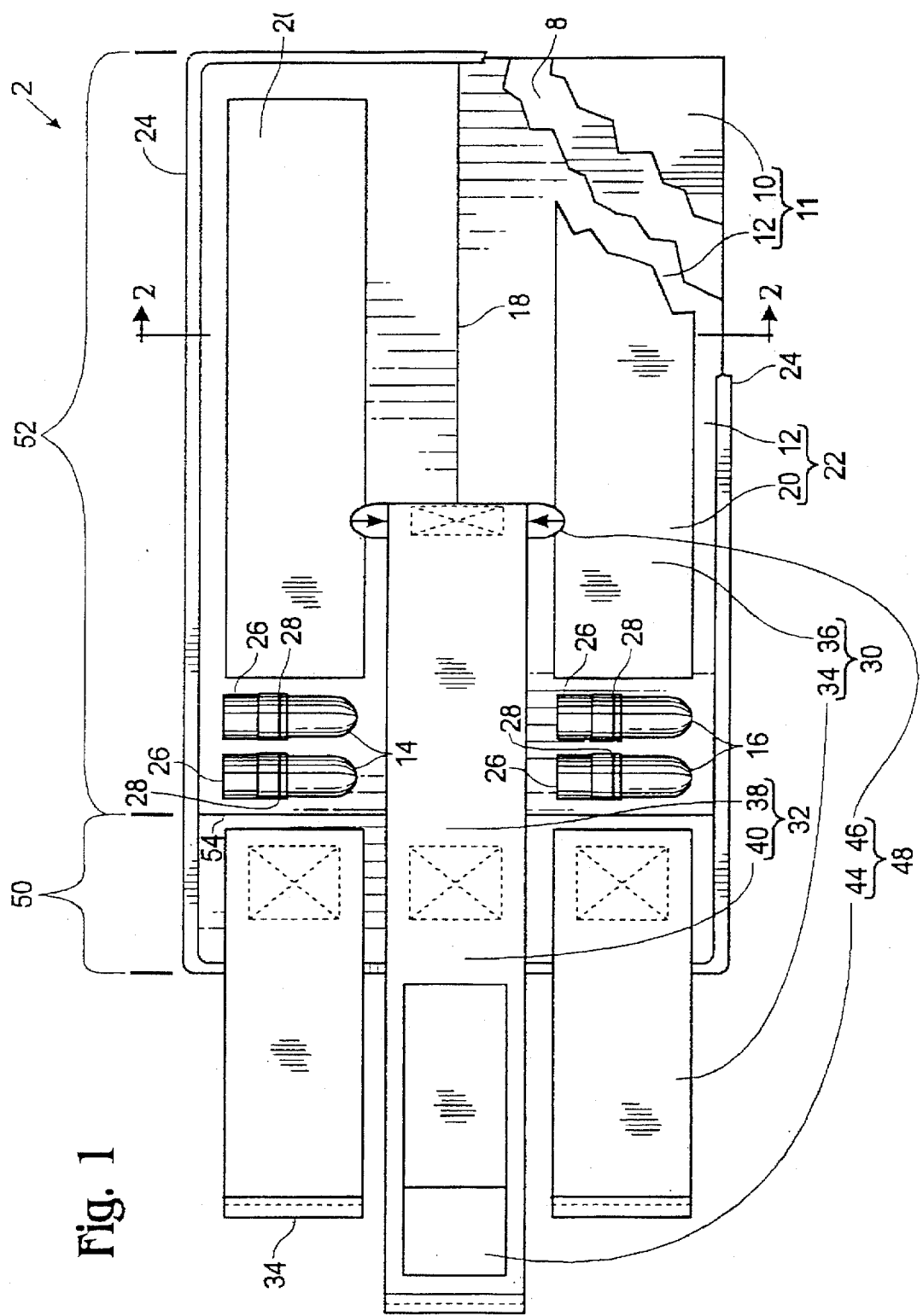
FIG. 1 is a plan view of the specific embodiment of the improved overlapping occlusive cuff for application to a limb substantially cylindrical in shape.

FIG. 1 is a plan view illustrating details of an overlapping occlusive cuff 2 having secondary safety securing means for improved safety. Cuff 2 is designed for best shape conformance to limbs substantially cylindrical in shape. Design and fabrication of cuff 2 is similar in certain respects to the design and fabrication of the invention disclosed by Robinette-Lehman in U.S. Pat. No. 4,635,635, but with a number of significant improvements resulting in enhanced safety, efficacy and cost-effectiveness, as herebelow described.

Also, Robinette-Lehman in U.S. Pat. No. 4,635,635 discloses six cuff sizes whereas, cuff 2 is fabricated in sizes of different length and in a variety of widths to fit 95% of the normal adult size range, so that the surgeon may optimally select cuff 2 by length and width depending on the patient's limb circumference, limb length and the surgical procedure.

As shown in FIG. 1, cuff 2 comprises inflatable bladders 4 and 6 having proximal and distal sides and two ends, wherein the length of the proximal and distal sides is sufficient for the bladder to encircle the limb at a desired location and overlap on itself in a substantially circumferential direction around the limb. Inflatable bladders 4 and 6 are contained in sheath 11 formed by layers 10 and 12, wherein the length of sheath 11 is sufficient for sheath 11 to encircle the limb at a desired location and overlap on itself in a substantially circumferential direction around the limb. Cuff 2 is fabricated using only three layers 8, 10 and 12 and has no internal thermoplastic stiffener. This characteristic results in a cuff design that is thinner and more flexible improving the performance of cuff 2 by providing a more uniform applied pressure to the limb in both the longitudinal axis along the limb as well as at the point where bladders 4 and 6 overlap reducing the number of potential paths for blood flow. This characteristic makes cuff 2 more suitable for pediatric patients with small limb circumferences than other cuffs which are thicker in cross-section. Layers 8, 10 and 12 of cuff 2 are fabricated from a flexible gas-impermeable synthetic cloth, such as a woven nylon backed with a thermoplastic polyurethane coating. This material is substantially inextensible when cuff 2 is pressurized up to 500 mmHg. Layer 12 and bottom layer 10 are coated with polyurethane on one side only and inside layer 8 is coated on both sides. Thermoplastic coatings on layers 8, 10 and 12 facilitate bonding or "heat sealing" in fabrication of cuff 2. The woven nylon surface of layer 10 is a soft, non-wrinkling material. Use of this softer material makes the wider embodiments of cuff 2 more comparable to blood pressure cuffs than other cuffs employing less compliant materials. The materials and fabrication technique of cuff 2 make it economically suitable for limited re-use applications. Other materials for layers 8, 10, and 12 such as flexible thermoplastic polyvinylchloride (PVC) sheeting may be readily substituted for design transferability of cuff 2 to disposable applications in which cuff 2 may be sterile or non-sterile.

Valve sets 14 and 16 consists of two thermoplastic right-angle valves. With respect to valve sets 14 and 16, one port of the set may serve as an opening for cuff inflation and deflation while the other port of the set may be used for sensing the gas pressure within cuff 2. This feature allows the surgical tourniquet system to detect pressure drops and occluding kinks in the pneumatic hose connecting the tourniquet regulator and cuff 2.

Figure 2:
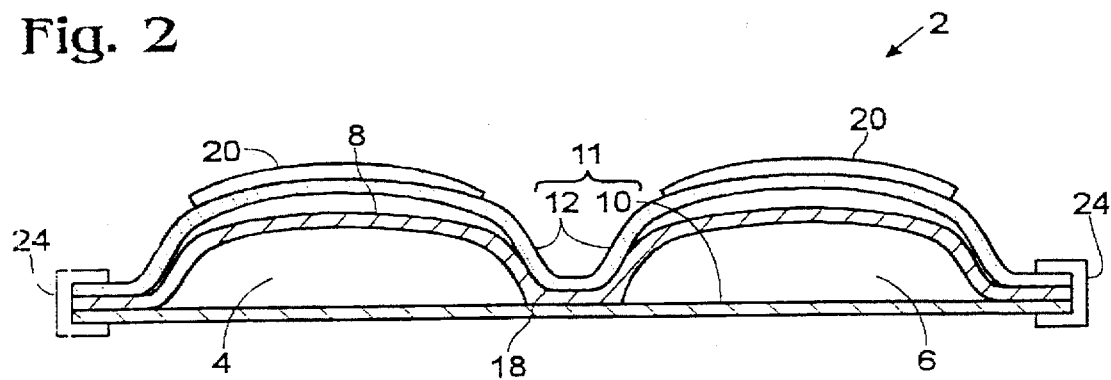
FIG. 2 is a cross-sectional view of the overlapping occlusive cuff of FIG. 1 taken along line 2—2.

Gas-impermeable inflation bladders 4 and 6 of cuff 2 are formed with bladder dividing heat seal 18 as illustrated in FIG. 2. Inflation bladders 4 and 6 form an integral part of cuff 2 and are not removable. Consequently, in cleaning and inspecting cuff 2 for re-use, errors in re-assembly which can affect safety and performance of cuff 2 have been eliminated.

Inclusion of bladder dividing heat seal 18 results in dual-bladder cuff 2 with bladder 4 permanently isolated from bladder 6. As shown in FIGS. 1 and 2, fluid access to bladder 4 is achieved by valve set 14 while fluid access to bladder 6 is through valve set 16. In another embodiment of the invention, omission of bladder dividing heat seal 18 results in a single-bladder cuff with one bladder 4. For the single-bladder cuff, fluid access to bladder 4 is achieved by valve set 14 as valve set 16 is omitted.

Referring to FIG. 1, loop material 20 on top layer 12 provides stiffening means in the form of compliant stiffening layer 22 comprised of woven plastic fibers and located above a segment of the overlapped bladders 4, 6 which covers the end of the overlapped bladders 4, 6 that is in closest proximity to the limb, for directing the bladder in the region of the overlap toward the limb when bladders 4, 6 are inflated. Stiffening layer 22 also secures sheath 11 around the limb when bladder 4 or 6 is inflated to a pressure sufficient to stop blood flow in the limb encircled by cuff 2. Layer 22 has a width dimension and a length dimension sufficient for encircling bladders 4 and 6 around the limb. The stiffness of layer 22 can by varied by selecting woven plastic fibers of different thickness and rigidity. The predetermined stiffness of layer 22 directs the portion of the bladder beneath layer 22 toward the limb to produce an applied pressure at predetermined levels near a plurality of predetermined locations on the limb beneath bladders 4 and 6 when bladders 4 and 6 are inflated. This arrangement is chosen to achieve a desired applied pressure gradient so that the risk of injury to nerves underlying cuff 2 is minimized. In addition, substitution of an internal die-cut, integrated thermoplastic stiffener with an external woven fiber stiffener layer 22 that is independent of the inflatable bladders 4 and 6 provides a cuff that is easier to apply and has superior consistency of blood flow occlusion with variations in technique of cuff application. This omission of the internal thermoplastic stiffener significantly reduces the cost to manufacture cuff 2 resulting in a cuff design that is more economical than the majority of tourniquet cuffs of the prior art.

Edge trim 24 consists of a synthetic cloth material such as nylon. Edge trim 24 protects the heat sealed areas of cuff 2 from damage in addition to preventing the rough edges of layers 8,10 and 12 from contacting the patient.

Pneumatic locking connectors 26 (PMC 26-04, Colder Products Co, St. Paul, Minn.) are inserted into the ports of valve sets 14 and 16. Each of the locking connectors 26 has a connecting element to connect bladders 4, 6 to a tube containing pressurized gas and a locking element with release means for locking bladders 4, 6 and the tube together. This arrangement maintains the passageway while allowing bi-directional rotation of the tube with respect to the connecting element. Luer connectors which are extensively used in prior art tourniquet cuffs are prone to accidental disconnection due to bi-directional rotation of the tube with respect to the connecting element. Use of locking connectors 26 reduce the risk of cuff deflation from accidental disconnection. Self-locking thermoplastic tie straps 28 secure connectors 26 in place.

Bladders 4 and 6 are held in place on a limb by bladder securing means 30 and secondary safety securing means 32 which are sufficient to secure bladders 4 and 6 around the limb when either bladder 4 or bladder 6 is inflated to a pressure sufficient to stop blood flow past cuff 2. Secondary safety securing means 32 functions independently of bladder securing means 30 such that bladders 4 and 6 remain overlapped and secured in a substantially circumferential direction if the bladder securing means 30 is not engaged or becomes ineffective while the bladder is inflated to a pressure sufficient to stop arterial blood flow into the limb distal to cuff 2. Bladder securing means 30 consists of hook material 34 and loop material 36. Secondary safety securing means 32, forming a separate and independent securing means from bladder securing means 30, is composed of loop material 38 and hook material 40. Hook material 40 and loop material 38 of secondary safety securing means 32 are different in color from the materials of bladder securing means 30 to distinguish secondary safety securing means 32 and to assist the user in applying cuff 2 to the patient.

Secondary safety securing means 32 also provides independent stiffening means, where each of the overlapping bladders 4 and 6 and the stiffening means overlaps on itself independently around the limb to direct the overlapped bladders 4 and 6 towards the limb and thereby improve application of pressure onto the limb beneath the overlap. This arrangement also allows the snugness of bladders 4 and 6 and snugness of the stiffening means on a limb to be selected independently by an operator. The stiffening means is comprised of woven plastic fibers having preselected stiffness. The selection of material for the stiffening means and the degree of extensibility of the material can be varied to produce applied pressures at predetermined levels near a plurality of predetermined locations on the limb beneath bladders 4 and 6 when bladders 4 and 6 are inflated.

Marking means 42 provides information useful to an operator in determining the pressure to which bladders 4 and 6 should be inflated to occlude blood flow. Marking means 42 comprises one element consisting of a set of graduated markings and another element consisting of a cursor mark whereby the value of a preselected parameter is estimated by the juxtaposition of the cursor mark and one of the set of graduated markings when the secondary safety securing means 32 is secured over the overlapping bladders 4 and 6 in a substantially circumferential direction around the limb. Marking means 42 consists of label 44 sewn to hook material 40 and pointer 46 sewn to the end of loop material 38. Pointer 46 is constructed of semi-rigid thermoplastic sheeting such as polypropylene with a thickness of approximately 1 mm and having a length sufficient to expose a printed arrow or similar indicator when second bladder securing means 32 encircles cuff 2.

Figure 3:
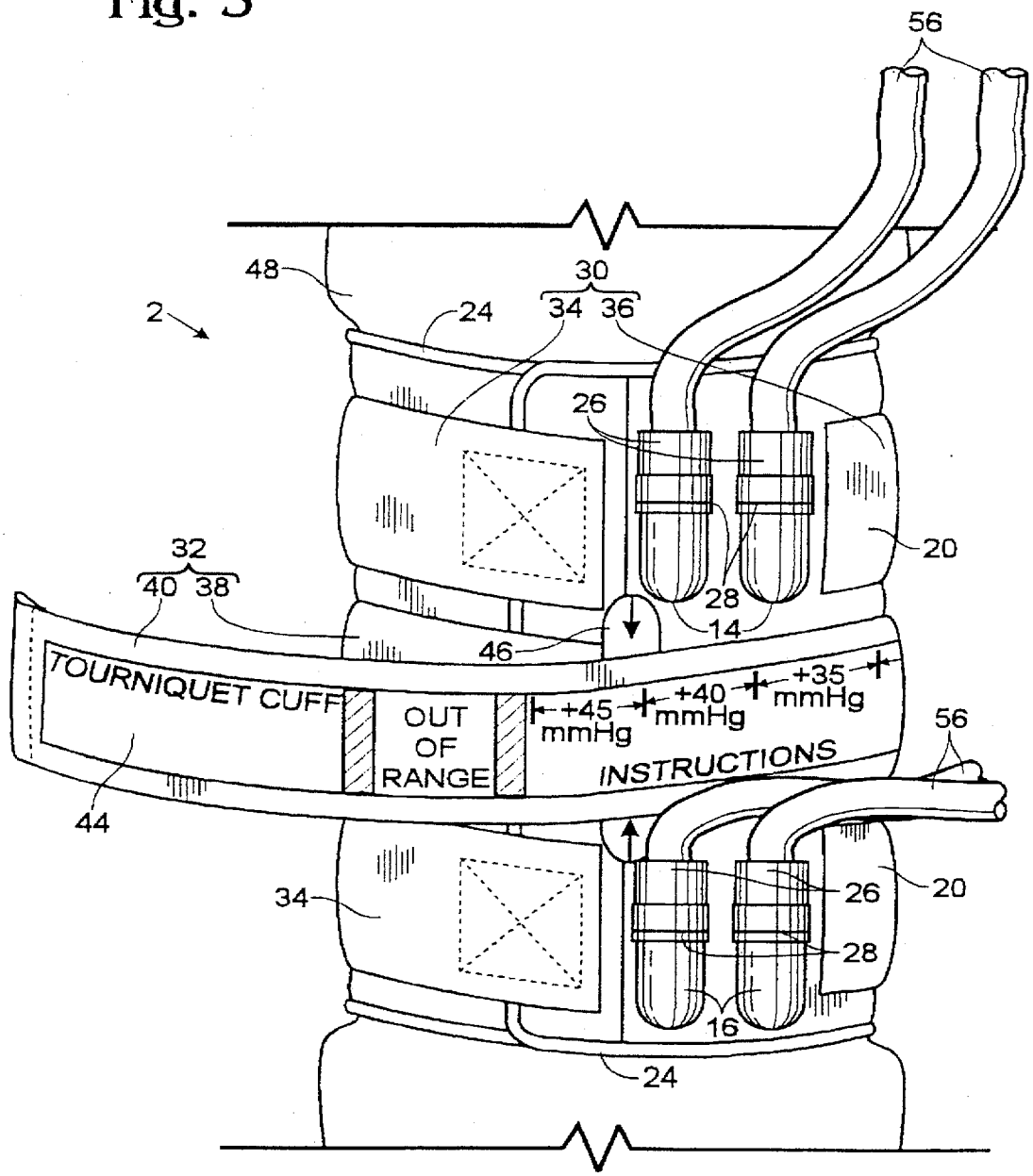
FIG. 3 is a pictorial representation of the overlapping occlusive cuff, secondary safety securing means and markings means shown in FIG. 1 as applied to a patient's limb.

FIG. 3 illustrates application of overlapping occlusive cuff 2 to substantially cylindrical limb 48. Label 44 includes markings to restrict use to properly trained staff, instructions detailing proper use of cuff 2 in intravenous regional anesthesia, index markings to identify size range or the maximum and minimum permissible limb circumferences, and a calibrated scale to indicate a recommended minimum inflation pressure for cuff 2 on limb 48. The recommended minimum inflation pressure corresponds to the lowest constant pressure normally required in cuff 2 to safely and reliably occlude blood flow over a time period suitably long for the performance of a surgical procedure when cuff 2 snugly encircles a normal limb of that circumference in a normotensive subject. This information enables the user to safely apply or determine if another tourniquet cuff size would be more appropriate for the patient and to select an inflation pressure for cuff 2 to reduce the risk of underlying nerve injury and achieve improved patient tolerance of cuff 2 when cuff 2 is pressurized.

Fabrication of the overlapping occlusive cuff 2 proceeds through manufacture of a number of subassemblies. First, layers 8, 10 and 12 are die cut from thermoplastic cloth material. At this time, circular openings are die cut into layers 8 and 12 for later passage of valve port sets 14 and 16. Loop material 20 is sewn to top layer 12 with loops facing away from layer 12. Valve sets 14 and 16 are inserted through the circular openings previously die cut into layer 8, and flanges of valve sets 14 and 16 are bonded to the bottom coated surface of layer 8 through use of radio frequency heat sealing equipment. Layers 8, 10 and 12 are then manipulated such that valve sets 14 and 16, previously bonded to layer 8, pass through the circular openings in layer 12, and the thermoplastic polyurethane coating of layer 12 contacts the upper coated surface of layer 8 and the thermoplastic polyurethane coating of layer 10 contacts the lower coated surface of layer 8. Following this step, layers 8, 10 and 12 are permanently bonded together at the peripheral edge of cuff 2, at the bladder dividing heat seal 18, and at fluid tight seal 54 through use of the radio frequency heat sealing equipment, thereby forming non-inflatable bladder section 50 and inflatable bladder section 52 contained within sheath 11 formed by layers 10 and 12. This completes the fabrication of the first subassembly.

The second subassembly, or secondary safety securing means 32, is fabricated as follows. Pointer 46 is die cut from polypropylene sheet material which has been previously silk screened with position indicators such as arrows in enamel ink. Label 44, previously silk screened with text in enamel ink, is die cut from nylon sheet material. Loop material 38 is sewn to hook material 40 such that the hooks face away from the loops and material 38 overlaps material 40 by 10 cm. Pointer 46 is then sewn to the end of loop material 38 and label 44 is sewn to the non-hook side of material 40.

In final assembly of cuff 2, edge trim 24 is first sewn around the perimeter of cuff 2 as shown in FIG. 1. Hook material 34 is sewn to the end of section 50 with the hooks facing towards layer 12. Secondary safety securing means 32 is sewn to section 50 such that the hooks of material 40 face layer 12 and the loops of material 38 face away from layer 12. The ends of hook materials 34 and 40 of bladder securing means 30 and 32 are folded over and sewn to provide a small flap for facilitating the release of bladder and secondary safety securing means 30 and 32 upon completion of the surgical procedure. Finally, connectors 26 are inserted into valve sets 14 and 16, and tie straps 28 are wrapped and tightened around valves sets 14 and 16 to secure connectors 26 in place. This completes fabrication of cuff 2.

As shown in FIG. 3, cuff 2 is applied to limb 48 with bladder securing means 30 being fastened followed by secondary safety securing means 32 being wrapped around cuff 2. Hook material 34 engages loop material 20. Adjustment of secondary safety securing means 32, which also functions as an independent stiffening means, allows the user to adjust the snugness of the stiffening means independent of the snugness of overlapped bladders 4 and 6, producing a variable spatial distribution of pressure on encircled limb 48 beneath overlapped bladders 4 and 6 of cuff 2. The user references label 44 to obtain the recommended minimum inflation pressure indicated by the position of pointer 46 with respect to calibrated scale on label 44. Should pointer 46 fall outside the calibrated scale, the user is instructed to select a different size of cuff for the patient. In FIG. 3, cuff 2 is connected by tubing 56 and connectors 26 to a pressure source providing gas at a regulated pressure between zero and 500 mmHg. This arrangement provides a means of inflating cuff 2 to apply a desired distribution of pressures to limb 48.

Through tubing 56, cuff 2 can be readily adapted for use with any of a number of systems having a pressure regulator which regulates the supply of pressurized gas to inflatable bladders 4 and 6 of cuff 2 in order to maintain the pressure applied to limb 48 by cuff 2 near a pressure sufficient to occlude flow in blood vessels in limb 48 distal to cuff 2 over a time period suitably long for the performance of a surgical procedure. Such systems are described in U.S. Pat. No. 4,469,099 and in pending having U.S. patent application Ser. No. 08/297,256, which patent and patent application are herein incorporated by reference.

DESCRIPTION OF THE ALTERNATE EMBODIMENT

The alternate embodiment illustrated is not intended to be exhaustive or to limit the invention to the precise form disclosed. It is chosen and described in order to explain the principles of the invention and its application and practical use, and thereby enable others skilled in the art to utilize the invention.

FIG. 4 is a plan view of the alternate embodiment. FIG. 4 illustrates details of an overlapping occlusive tourniquet cuff 58 having secondary safety securing means for improved safety. Cuff 58 is designed for best shape conformance to limbs substantially conical in shape. As with cuff 2, cuff 58 is fabricated in a range of lengths and widths designed to fit 95% of the normal adult size range, so that the surgeon may optimally select cuff 58 by length and width depending on the patient's limb circumference, limb length and the surgical procedure.

Design and fabrication of cuff 58 is similar in certain respects to the design and fabrication of the invention disclosed by Robinette-Lehman in the U.S. Pat. No. 4,635,635, but with a number of significant improvements resulting in enhanced safety, efficacy and cost-effectiveness, as herebelow described.

FIG. 4 illustrates an inflatable overlapping occlusive tourniquet cuff 58 for application to limbs substantially conical in shape. Cuff 58 has a substantially arcuate shape with the radius of the arc passing along the width dimension. Cuff 58 has a radial length dimension of 88 cm measured along the centerline of cuff 58 and a width dimension of 20 cm perpendicular to the centerline.

As shown in FIG. 4, cuff 58 comprises inflatable bladders 74 and 76 having proximal and distal sides and two ends, wherein the length of the proximal and distal sides is sufficient for the bladder to encircle the limb at a desired location and overlap on itself in a substantially circumferential direction around the limb. Inflatable bladders 74 and 76 are contained in sheath 61 formed by layers 60 and 64, wherein the length of sheath 61 is sufficient for sheath 61 to encircle the limb at the desired location and overlap on itself in a substantially circumferential direction around the limb. Cuff 58 is fabricated using only three layers 60, 62 and 64 and has no internal thermoplastic stiffener. This characteristic results in a cuff design that is thinner and more flexible improving the performance of cuff 58 by providing a more uniform applied pressure to the limb in both the longitudinal axis along the limb as well as at the point where bladders 74 and 76 overlap reducing the number of potential paths for blood flow. This characteristic makes cuff 58 more suitable for pediatric patients with small limb circumferences than other cuffs which are thicker in cross-section. Layers 60, 62 and 64 of cuff 58 are fabricated from a flexible gas-impermeable synthetic cloth such as a woven nylon backed with a thermoplastic polyurethane coating. This material is substantially inextensible when cuff 58 is pressurized up to 500 mmHg. Layer 60 and bottom layer 64 are coated with polyurethane on one side only, and inside layer 62 is coated on both sides. Thermoplastic coatings on layers 60, 62 and 64 facilitate bonding or "heat sealing" in fabrication of cuff 58. The woven nylon surface of layer 64 is a soft, non-wrinkling material. Use of this softer material makes the wider embodiments of cuff 58 more comparable to blood pressure cuffs than other cuffs employing less compliant materials. The materials and fabrication technique of cuff 58 make it economically suitable for limited re-use applications. Other materials for layers 60, 62 and 64 such as flexible thermoplastic polyvinylchloride (PVC) sheeting may be readily substituted for design transferability of cuff 58 to disposable applications in which cuff 58 may be sterile or non-sterile.

Valve sets 66 and 68 consist of two thermoplastic right-angle valves. With respect to valve sets 66 and 68, one port of the set may serve as an opening for cuff inflation and deflation while the other port of the set may be used for sensing the gas pressure within cuff 58. This feature allows the surgical tourniquet system to detect pressure drops and occluding kinks in the pneumatic hose connecting the tourniquet regulator and cuff 58.

Gas-impermeable inflation bladders 74 and 76 of cuff 58 are formed with bladder dividing heat seal 78 as illustrated in FIG. 4. Bladder dividing heat seal 78 is an arcuate sinusoidal wave of a predefined frequency and amplitude which runs parallel to the centerline of cuff 58. Inflation bladders 74 and 76 form an integral part of cuff 58 and are not removable. Consequently, in cleaning and inspecting cuff 58 for re-use, errors in re-assembly which can affect safety and performance of cuff 2 have been eliminated.

Inclusion of bladder dividing heat seal 78 results in dual-bladder cuff 58 with bladder 74 permanently isolated from bladder 76. As shown in FIGS. 4 and 5, fluid access to bladder 74 is through valve set 66 while fluid access to bladder 76 is through valve set 68. In another embodiment of the invention, omission of heat seal 78 results in a single-bladder cuff with one bladder 74. For the single-bladder cuff, fluid access to bladder 74 is achieved by valve set 66 as valve set 68 is omitted.

Referring to FIG. 4, loop material 70 on top layer 60 provides stiffening means in the form of compliant stiffening layer 72 comprised of woven plastic fibers and located above a segment of the overlapped bladders 74 and 76. Stiffening layer 72 which covers the end of the overlapped bladders 74 and 76 that is in closest proximity to the limb directs the bladders in the region of the overlap toward the limb when bladders 74 and 76 are inflated. Stiffening layer 72 also secures sheath 61 around the limb when bladder 74 or 76 is inflated to a pressure sufficient to stop blood flow in the limb encircled by cuff 58. Layer 72 has a width dimension and a length dimension sufficient for encircling bladders 4 and 6 around the limb. The stiffness of layer 22 can by varied by selecting woven plastic fibers of different thickness and rigidity. The predetermined stiffness of layer 72 directs the portion of the bladder beneath layer 72 toward the limb to produce applied pressures at predetermined levels near a plurality of predetermined locations on the limb beneath bladders 74 and 76 when bladders 74 and 76 are inflated. The selection of materials for the stiffening means and the degree of extensibility of the material can be varied to produce a desired applied pressure on the limb. This arrangement is chosen to achieve a desired applied pressure gradient so that the risk of injury to nerves underlying cuff 58 is minimized. In addition, substitution of an internal die-cut, integrated thermoplastic stiffener with an external woven fiber stiffener layer 72 that is independent of the inflatable bladders 74 and 76 provides a cuff that is easier to apply and has superior consistency of blood flow occlusion with variations in technique of cuff application. This omission of the internal thermoplastic stiffener significantly reduces the cost to manufacture cuff 58 resulting in a cuff design that is more economical than the majority of tourniquet cuffs of the prior art.

Partial fluting means comprised of a plurality of seams located at preselected distances from the two end edges of the bladders 74 and 76 controls the expansion of bladders 74 and 76 when cuff 58 is inflated. Partial flutes 80 are positioned to overlap both layer 60 and the edge of loop material 70 and are heat sealed to permanently bond layers 60, 62, 64 and 70 together thereby preventing expansion of bladders 74 and 76 within the region of the partial flutes 80. The frequency of the partial flutes 80 on the proximal and distal edges of cuff 58 reduces the tendency of cuff 58 to rolling down the limb when bladders 74 and 76 of cuff 58 are pressurized.

As shown in FIGS. 4 and 7, cuff 58 of this alternate embodiment is designed for best conformance to limb 58 where limb 58 is conical or tapered in shape. In this embodiment, the frequency (i.e. the number and location) of partial flutes 80, as well as the shapes and sizes of partial flutes 80, are predetermined to maintain layers 60 and 64 in fixed position relative to one another in the regions of the partial flutes, thus to reduce the tendency of bladders 74 and 76 to roll down limb 106 and to apply a desired distribution of pressures to limb 106. Partial flutes 80 constrain the shape and volume of bladders 74 and 76 when inflated, thus reducing the time required to inflate to, and deflate from, a desired pressure.

When the size and shape of cuff 58 of this embodiment are selected so that cuff 58 fits thighs, partial flutes 80 are formed by making four circular heat seals, approximately 2-cm in diameter, spaced at substantially equal distances along the proximal and distal sides of cuff 58, to bond layers 60 and 64 together in circular shapes which extend into bladders 74 and 76. Partial flutes 80 are thus shaped as circles in this embodiment, to reduce the stresses around the edges of the partial flutes 80 when bladders 74 and 76 are pressurized, and the 2-cm diameter of partial flutes 80 was selected to reduce wrinkling in bladders 74 and 76, and corresponding wrinkling of the skin and tissue in limb 106 beneath layer 64, when bladders 74 and 76 are pressurized.

In this embodiment, when designing cuff 58 for a specified range of limb sizes or shapes, or to alter the distribution of pressures applied to the limb, or to reduce the tendency of bladders 74 and 76 to roll down encircled limb 106, or to achieve optimal reduction or roll tendency when only a single-bladder cuff is required, the shape, size, number, and location of each of the partial flutes 80 can be optimized. For example, when a single bladder cuff of this embodiment was fabricated as described elsewhere in this specification, improved cuff performance was found to be achieved with four partial flutes 80 extending from the proximal side of cuff 58, and four partial flutes 80 extending from the distal side of cuff 58, spaced at equal distances along the sides, wherein each of the partial flutes 80 had a substantially elongated shape, the length of each extending generally perpendicular to the side edges toward the center of the bladder between the side edges, had a rounded end to reduce stress and wrinkling, had a width of about 3-mm, and had a length of less than half of the width of bladder 74 at its location.

In the specified embodiment described in another section of this specification, for limbs which are substantially cylindrical in shape, partial flutes can also be included if desired for improved performance and stability.

Edge trim 82 consists of synthetic cloth material such as nylon. Edge trim 82 protects the heat sealed areas of cuff 58 from damage in addition to preventing the rough edges of layers 60, 62, and 64 from contacting the patient.

Pneumatic locking connectors 84 (PMC 26-04, Colder Products Co, St. Paul, Minn.) are inserted into the ports of valve sets 66 and 68. Each of the locking connectors 84 has a connecting element to connect bladders 74 and 76 to a tube containing pressurized gas and a locking element with release means for locking bladders 74 and 76 and the tube together. This arrangement maintains the passageway while allowing bidirectional rotation of the tube with respect to the connecting element. Luer connectors which are extensively used in prior art tourniquet cuffs are prone to accidental disconnection due to bi-directional rotation of the tube with respect to the connecting element. Use of locking connectors 84 reduces the risk of cuff deflation from accidental disconnection. Self-locking thermoplastic tie straps 86 secure connectors 84 in place.

Tie straps 86 are selected to hav physical size and strength characteristics sufficient to non-releasably attach connectors 84 to valve sets 66 and 68 and to the tubes containing pressurized gas, so that gas-tight passageways are maintained despite large pulling forces along the longitudinal axis of the tubes which are greater than those encountered in surgical procedures.

Each locking connector 84 thus includes one component non-releasably attached to a valve and a second component non-releasably attached to a tube. In operation, the gas-tight passageway is established by linear translation of the components toward each other. The locking element and release means of each locking connector 84 holds the two components together until the release means is actuated manually and a detaching force above a predetermined detachment threshold is then applied to the tube along the longitudinal axis of the tube.

The physical size and shape (e.g. diameters and lengths) of the first component of each connector 84, which is non-releasably attached to each valve in valve set 66 and 68, is selected so that the first component mates only with a tube to which is attached the second component of connector 84, having a size and shape which allows it to couple with the first component to establish a gas-tight passageway. In this manner, increased safety is achieved because the selected physical characteristics of the components of connectors 84, which are non-releasably attached to cuff 58, prevent inadvertent errors in attachment, including inadvertent attachment of connectors 84 of cuff 58 to any of the tubes commonly found in operating rooms which have Luer lock connectors. Also, if desired for improved safety, when using dual-bladder cuff 58, the physical size and shape of the components of connectors 84 in valve set 66 for bladder 74 can be selected to be different from the physical shape and size of the components of connectors 84 in valve set 68 for bladder 76, thus preventing inadvertent errors in matching tubes to bladders in dual-bladder cuff 58. This substantially increases safety when cuff 58 is used for Bier block anesthesia.

Bladders 74 and 76 are held in place on a limb by bladder securing means 88 and secondary safety securing means 90 which are sufficient to secure bladders 74 and 76 around the limb when either bladder 74 or bladder 76 is inflated to a pressure sufficient to stop blood flow past cuff 58. Secondary safety securing means 90 functions independently of bladder securing means 88 such that bladders 74 and 76 remain overlapped and secured in a substantially circumferential direction if the bladder securing means 88 is not engaged or becomes ineffective while the bladder is inflated to a pressure sufficient to stop arterial blood flow into the limb distal to cuff 58.

Bladder securing means 88 consists of hook material 92 and loop material 70 as shown in FIG. 4 and FIG. 6. Secondary safety securing means 90, forming a separate and independent securing means from bladder securing means 88, is composed of loop material 70, hook material 94, attachment loops 96 and 98, and reinforced thermoplastic rings 100. Rings 100 of secondary safety securing means 90 allow hook material 94 to pivot and engage loop material 70 over a range of angles with respect to the centerline of cuff 58. Rings 100 are D-shaped and are injection molded from a plastic resin impregnated with reinforcing agents such as glass or carbon fiber. Loops 96 and 98 of secondary safety securing means 90 consist of layers 102 and 104 are fabricated from a thermoplastic polyurethane coated synthetic cloth similar to the material of layer 60.

FIG. 7 illustrates application of overlapping occlusive cuff 58 to substantially conical limb 106. Markings which include label 108 and inflation and alignment guide 110 include markings to restrict use of cuff 58 to properly trained staff, application instructions for securing cuff 58 around limb 106 and instructions detailing proper use of cuff 58 in intravenous regional anesthesia.

Marking means consisting of inflation and alignment guide 110 and label 112 provide information useful to an operator in determining the pressure to which bladders 74 and 76 should be inflated to occlude blood flow. Marking means comprises one element consisting of a set of graduated markings printed on label 112 and another element consisting of a cursor mark located on inflation and alignment guide 110 whereby the value of a preselected parameter is estimated by the juxtaposition of the cursor mark and one of the set of graduated markings when the secondary safety securing means 90 is secured over the overlapping bladders 74 and 76 in a substantially circumferential direction around the limb. Label 112 attached to loop material 70 also includes index markings to identify size range or the maximum and minimum permissible limb circumferences that cuff 58 can be adjusted to fit, and a calibrated scale to indicate a recommended minimum inflation pressure for cuff 58 when applied to limb 106. The recommended minimum inflation pressure corresponds to the lowest constant pressure normally required in cuff 58 to safely and reliably occlude blood flow over a time period suitably long for the performance of a surgical procedure when cuff 58 snugly encircles a normal limb of that circumference in a normotensive subject. This information enables the user to safely apply or determine if another tourniquet cuff size would be more appropriate for the patient and to select an inflation pressure for cuff 58 to reduce the risk of underlying nerve injury and achieve improved patient tolerance of cuff 58 when cuff 58 is pressurized.

Fabrication of the overlapping occlusive cuff 58 proceeds through manufacture of a number of subassemblies. First, layers 60, 62 and 64 are die cut from thermoplastic cloth material. At this time, circular openings are die cut into layers 60 and 62 for later passage of valve port sets 66 and 68.

Label 112, previously silk screened with maximum and minimum permissible limb circumferences and a calibrated scale to indicate a recommended minimum pressure for cuff 58 in enamel ink, is sewn to the loop side of loop material 70. Loop material 70 is sewn to top layer 60 with loops facing away from layer 60. Valve sets 66 and 68 are inserted through the circular openings previously die cut into layer 62, and flanges of valve sets 66 and 68 are bonded to the bottom coated surface of layer 62 through use of radio frequency heat sealing equipment. Layers 60, 62 and 64 are then manipulated such that valve sets 66 and 68, previously bonded to layer 62, pass through the circular openings in layer 60, and the thermoplastic polyurethane coating of layer 60 contacts the upper coated surface of layer 62 and the thermoplastic polyurethane coating of layer 64 contacts the lower coated surface of layer 62. Following this step, layers 60, 62 and 64 are permanently bonded together at the peripheral edge of cuff 58, at the bladder dividing heat seal 78, and at fluid tight seal 118 through use of the radio frequency heat sealing equipment, thereby forming non-inflatable section 114 and inflatable bladder section 116 contained within sheath 61 formed by layers 60 and 64.

Partial fluting means 80 bonding layers 60,62 and 64 together using heat seals of either circular or D shaped configuration having an outside diameter of 1.57 cm and inside diameter of 1.19 cm, are formed through use of the radio frequency heat sealing equipment. This completes the fabrication of the first subassembly.

The second subassembly, or secondary safety securing means 90, is fabricated as follows. Labels 108, previously silk screened with text in enamel ink and die cut from nylon cloth material is sewn to the non-hook side of hook material 94. The ends of hook materials 94 of secondary safety securing means 90 are folded over and sewn to provide a small flap for facilitating the release of secondary safety securing means 90 upon completion of the surgical procedure. Assemblies 96 and 98 of secondary safety securing means 90 shown in FIGS. 4 and 6 are constructed by bonding die cut layers 102 and 104 together when the polyurethane coatings of layers 102 and 104 are in contact. Bonded layers 102 and 104 are then passed through rings 100 to form assembly 96 which is sewn to hook material 94 as shown in FIG. 6. Hook material 94 is sewn to assembly 96 such that hooks of material 94 face towards cuff 58.

In final assembly of overlapping occlusive cuff 58, edge trim 82 is first sewn around the perimeter of cuff 58 as shown in FIG. 4. Hook material 92 of bladder securing means 88 is sewn to non-coated surface of layer 64 in section 114 of cuff 58 with hooks facing away from layer 64 as shown in FIGS. 4 and 6. Inflation and alignment guide 110 is sewn to non-coated surface of layer 60 in section 114 of cuff 58. As shown in FIG. 6, secondary safety securing means assembly 90 forming a separate and independent securing means from bladder securing means 88 is completed by passing bonded layers 102 and 104 through rings 100 to form assembly 98 and sewn to layer 60 located in section 114 of cuff 58 such that hooks of material 94 face towards cuff 58. Finally, locking connectors 84 are inserted into valve sets 66 and 68, and tie straps 84 are wrapped and tightened around valves sets 66 and 68 to secure locking connectors 84 in place. This completes fabrication of overlapping occlusive cuff 58.

As shown in FIG. 7, cuff 58 is applied to limb 106 with bladder securing means 88 being fastened followed by secondary safety securing means 90. Bladder securing means 88 is secured around limb 106 by hook material 92 engaging loop material 70. Secondary safety securing means 90 is utilized by pivoting hook material 94 and also engaging loop material 70 such that a maximum contact area is achieved. The arcuate shape of cuff 58 and bladder securing means 88 provides conformance adjustment means for adjusting the shape of cuff 58 over a predefined range of tapers so that cuff 58 remains substantially in contact with limb 106 along the width of cuff 58 and circumference of limb 106. This conformance adjustment means increases resistance of cuff 58 to sudden telescoping down limb 106 due to shape mismatch. Inflation and alignment guide 110 indicates to the user the predefined range of tapers to which cuff 58 can conform by specifying that guide 110 must lie between the proximal and distal edges of cuff 58 when cuff 58 is snugly applied to limb 106. The user references label 112 to obtain the recommended minimum inflation pressure indicated by the position of inflation and alignment guide 110 with respect to calibrated scale of label 112. Should inflation and alignment guide 110 fall outside the calibrated scale on label 112, the user is instructed to select a different size of cuff for the patient. In FIG. 7, cuff 58 is connected by tubing 120 and locking connectors 84 to a pressure source providing gas at a regulated pressure between zero and 500 mmHg. This arrangement provides a means of inflating cuff 58 to apply a desired distribution of pressures to limb 106.

It is to be understood that the invention is not to be limited to the details herein given but may be modified within the scope of the appended claims.

The invention claimed is:

1. An overlapping tourniquet cuff system comprising:

an inflatable bladder having a length selected to be greater than the circumference of a limb at a desired location;

a sheath containing the bladder and having an inner side adapted to face the limb, an outer side adapted to face away from the limb and a length greater than the length of the bladder, thereby establishing an inflating portion and a non-inflating portion of the sheath along the length of the sheath;

first sheath securing means having a first element on the outer side of the sheath, and a second element attached to the inner side of the sheath at a selected location on the non-inflating portion so that the second element engages the first element to secure the sheath when the sheath is applied around the limb;

second sheath securing means for securing the overlapping sheath in a substantially circumferential direction around the limb such that the sheath remains overlapped and secured if the second element of the first sheath securing means does not engage the first element of the first sheath securing means or becomes ineffective while the bladder is inflated to a pressure sufficient to occlude flow in blood vessels in the limb encircled by the sheath, and wherein the length of the sheath is sufficient for the inflating portion to overlap upon itself and for the non-inflating portion of the sheath to overlap the inflating portion when the sheath is applied circumferentially around the limb at the desired location, with the first and second sheath securing means securing the sheath around the limb; and pressure regulator means adapted to supply the inflating portion of the sheath with pressurized gas.

2. The overlapping tourniquet cuff system as described in claim 1 wherein the pressure regulator means supplies the gas at a pressure less than 500 mmHg.

3. The overlapping tourniquet cuff system as described in claim 1 wherein the pressure regulator means supplies the gas at a pressure sufficient to occlude flow in blood vessels in the limb encircled by the sheath.

4. The overlapping tourniquet cuff system as described in claim 3 wherein the pressure regulator means further supplies the pressurized gas over a time period suitably long for the performance of a surgical procedure on the limb distal to the sheath.

5. The overlapping tourniquet cuff system as described in claim 1 wherein the sheath includes side edges, end edges, a center axis located equidistant between the side edges, and a length dimension along the center axis between the end edges, and wherein the second sheath securing means has a first securing element attached to the outer side of the sheath across the center axis and a second securing element attached to the outer side of the sheath across the center axis and extending past one of the end edges to engage the first securing element when the sheath is applied around the limb at the desired location, thereby securing the sheath.

6. An overlapping tourniquet cuff system comprising:

a sheath having an inner side, an outer side, side edges, end edges, a center axis located equidistant between the side edges and a length dimension along the center axis between the end edges, and having an inflating portion and a non-inflating portion extending along the length of the sheath, wherein the length of the sheath is sufficient for the sheath to overlap when the sheath is applied circumferentially around a limb at a desired location;

first sheath securing means having a first element on the outer side of the sheath and a second element attached to the inner side of the sheath at a selected location in the non-inflating portion and extending across the center axis at the location so that the second element engages the first element to secure the sheath when the sheath is applied around the limb;

second sheath securing means for securing the overlapping sheath in a substantially circumferential direction around the limb such that the sheath remains overlapped and secured if the second element of the first sheath securing means does not engage the first element of the first sheath securing means or becomes ineffective while the inflating portion of the sheath is inflated to a pressure sufficient to occlude flow in blood vessels in the limb encircled by the sheath; and pressure regulator means adapted to supply the inflating portion of the sheath with pressurized gas.

7. The overlapping tourniquet cuff system as described in claim 6 wherein the pressure regulator means supplies the gas at a pressure between zero and 500 mmHg.

8. The overlapping tourniquet cuff system as described in claim 6 wherein the pressure regulator means supplies the gas at a pressure sufficient to occlude flow in blood vessels in the limb encircled by the sheath.

9. The overlapping tourniquet cuff system as described in claim 6 wherein the pressure regulator means further supplies the pressurized gas over a time period suitably long for the performance of a surgical procedure on the limb distal to the sheath.

10. The overlapping tourniquet cuff system as described in claim 6 wherein the second sheath securing means has a first securing element attached to the outer side of the sheath across the center axis and a second securing element attached to the outer side of the sheath across the center axis and extending past one of the end edges to engage the first securing element when the sheath is applied around the limb at the desired location, thereby securing the sheath.

11. An overlapping tourniquet cuff system having secondary securing means for improved safety, comprising:

a sheath having an inner side, an outer side, side edges, end edges, a center axis located equidistant between the side edges and a length dimension along the center axis between the end edges, and having an inflating portion and a non-inflating portion extending along the length of the sheath, wherein the length of the inflating portion of the sheath is sufficient for the inflating portion to overlap when the sheath is applied circumferentially around a limb at a desired location on the limb;

first sheath securing means having a first element on the outer side of the sheath and a second element on the inner side of the sheath at a selected sheath location and extending across the center axis at the location so that the second element engages the first element to secure the sheath when the sheath is applied around the limb, wherein the second element has a width dimension between the side edges which is not greater than the distance between the side edges at the selected sheath location and a length dimension along the center axis which is not greater than the width dimension; and second sheath securing means having a third element on the outer side of the sheath across the center axis of the sheath and having a fourth element attached to the outer side of the sheath across the center axis and extending past one of the end edges to engage the third element across the center axis of the sheath when the sheath is applied around the limb at the desired location, thereby securing the overlapping sheath in a substantially circumferential direction around the limb such that the sheath remains overlapped and secured if the second element of the first securing means does not engage or becomes ineffective while the inflating portion of the sheath is inflated to a pressure sufficient to occlude flow in blood vessels in the limb encircled by the sheath.

12. The overlapping tourniquet cuff system as described in claim 11 and including pressure regulator means adapted to supply the inflating portion of the sheath with pressurized gas.

13. The overlapping cuff system as described in claim 12 wherein the pressure regulator means supplies the pressurized gas at a pressure less than 500 mmHg.

14. The overlapping tourniquet cuff system as described in claim 12 wherein the pressure regulator means supplies the gas at a pressure sufficient to occlude flow in blood vessels in the limb encircled by the sheath.

15. The cuff as described in claim 12 wherein the pressure regulator means supplies the gas at a pressure sufficient to occlude flow in blood vessels in the limb distal to the sheath over a time period suitably long for the performance of a surgical procedure on the limb distal to the sheath.

* * * * *